United States Patent [19]

Austin et al.

[11] 4,152,513

[45] May 1, 1979

[54] PREPARATION OF ALKYL GLYCOSIDES OF AMINO SUGARS

[75] Inventors: Paul R. Austin, Wilmington; George A. Reed, Newark, both of Del.

[73] Assignee: University of Delaware, Newark, Del.

[21] Appl. No.: 802,424

[22] Filed: Jun. 1, 1977

[51] Int. Cl.$^2$ .................... C07H 15/02; C07H 5/06
[52] U.S. Cl. ......................... 536/4; 424/180; 536/18; 536/53
[58] Field of Search ............... 536/4, 18, 53

[56] References Cited

U.S. PATENT DOCUMENTS

| | | |
|---|---|---|
| 2,049,758 | 8/1936 | Bertsch et al. ............ 536/4 |
| 2,276,621 | 3/1942 | Langlois ................... 536/4 |
| 2,792,388 | 5/1957 | Ruelius .................... 536/53 |
| 3,296,245 | 1/1967 | Kaiser et al. .............. 536/4 |
| 3,375,243 | 3/1968 | Nevin et al. ............... 536/4 |
| 4,057,684 | 11/1977 | Kimura et al. ............. 536/53 |

*Primary Examiner*—Johnnie R. Brown

[57] ABSTRACT

A method for controlling the anomer ratio in alkyl glycosides of amino sugars produced by heating an N-acylamino sugar with an alcohol in the presence of an acidic catalyst comprising the continuous removal of byproduct water from the reaction zone.

2 Claims, No Drawings

PREPARATION OF ALKYL GLYCOSIDES OF AMINO SUGARS

BACKGROUND OF THE INVENTION

The Government of the United States has rights in this invention pursuant to Grant No. 04-6-158-44120 from the Department of Commerce.

1. Field of the Invention

This invention relates to a method for preparing alkyl glycosides of amino sugars.

2. Description of the Prior Art

Simple derivates of N-acetylglucosamine, the alkyl glucosaminides, alkyl 2-acetamidoglycopyranosides, or the alkyl glycosides of amino sugars as they are also called, are known to promote the growth of *Lactobacillus bifidus* (Zilliken, Archives of Biochemistry and Biophysics, 54, 392, 1954). In this application the β-anomer,

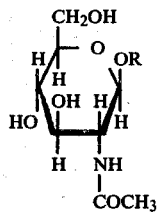

has been found to be the active substance, whereas the α-anomer,

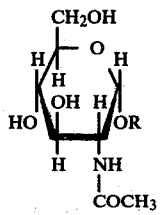

shows little or no activity (Poupard, Bacteriological Review, 37, 136, 1973).

The most commonly used method for the preparation of alkyl glycosides of amino sugars is the Fischer method which involves a one-step, acid-catalyzed reaction of the parent sugar with an appropriate alcohol (Langlois, Methods in Carbohydrate Chemistry, Whistler and Wolfrom, Eds., Academic Press, New York, 1963, Vol. 2, p. 83). This method produces good yields (70–80%) of the alkyl glucosaminide. However, the α-anomer predominates in the product and this is of little value in promoting growth of *L. bifidus*.

An alternate method of preparation is the Koenigs-Knorr method which involves a multi-step reaction with formation of the glycosyl halide as an intermediate (Conchie and Levvy, Methods in Carbohydrate Chemistry, ibid., p. 332). This method is more time-consuming and the yields of the alkyl glucosaminides are relatively low, but it has the advantage of producing larger proportions of the β-anomer.

The use of azeotropic distillation to remove water formed in the reaction of anhydrous alcohol with simple hemi-acetals is known (Smith and Cristol, Organic Chemistry, Reinhold Publishing Corporation, New York, 1966, p. 400). However, there is no teaching or suggestion that such a process would influence the proportion of the complex chiral α- and β-anomers formed in the synthesis of alkyl glycosides of amino sugars. Furthermore, there is no suggestion that the process would be successful in forming alkyl glycosides in the presence of competing hydroxyl groups in the amino sugars.

There is, therefore, a distinct need for a method of preparing alkyl glycosides of amino sugars which results in improved proportions of the β-anomers in the reaction products, and such a method is a primary object of this invention.

It is a further object to provide a process for preparing alkyl glycosides of amino sugars requiring shorter reaction times, and which minimizes the caramelization of the amino sugars.

SUMMARY OF THE INVENTION

The process of this invention comprises reacting an N-acylaminosugar with an excess of a lower aliphatic alcohol in the presence of an acidic catalyst at an elevated temperature in a reaction vessel fitted with means for continuously removing from the reaction zone the water that forms as a byproduct. The continuous removal of the byproduct water as it is formed is essential for production of alkyl glycosides of amino sugars containing maximum proportions of the β-anomers. In this process the rapid removal of byproduct water is accomplished (a) by distillation of the azeotrope of water with a reactant alcohol, which boils at a lower temperature than the alcohol itself, or (b) by distillation of a mixture of water with an alcohol which does not form an azeotrope with water, in which the vapor pressure of the water is a substantial proportion of the total vapor pressure.

In a preferred embodiment of the invention the reaction is carried out at a temperature between 30° and 100° C. in a reaction vessel fitted with a fractionating column so as to distill from the reaction mixture the byproduct water as it forms.

In another embodiment the reaction is carried out in distillation apparatus under reduced pressure in order to lower the temperature required for distillation of the byproduct water from the reaction mixture. This embodiment permits the use of higher boiling alcohols, reduces the time of reaction, and minimizes self-condensation, caramelization of the amino sugar, and the formation of undesired byproducts.

Examples of N-acylpyranosamines that are operable in the process of this invention include N-acetyl-D-glucosamine, N-propionyl-D-glucosamine, N-butyryl-D-glucosamine, N-acetyl-D-galactosamine, and N-acetyl-D-mannosamine.

Lower aliphatic alcohols, e.g. those having 1 to 4 carbon atoms, are especially preferred for use in this process. Specific alcohols that are operable include methanol, ethanol, 1-propanol, 2-propanol, 1-butanol, 2-butanol, 2-methyl-1-propanol and 2-methyl-2-propanol. The primary alcohols are most active in the process but secondary and tertiary alcohols can be used if desired. The amount of alcohol used is not critical except that a sufficent amount, e.g. 10–25 times the weight of the amino sugar is used to provide a workable reaction medium. Alcohols that form azeotropic mixtures with water are especially suitable. These include ethanol, the propanols and the butanols. The following Table I lists lower saturated alcohols that form azeotropes with water. The boiling points of the alcohols and their azeotropes are also given, together with ratios of alcohol to water in the azeotropes.

TABLE I

Alcohol-Water Azeotropes

| Alcohol | Boiling Point of Alcohol °C. | Boiling Point of Azeotrope °C. | Ratio of Alcohol to Water in Azeotrope |
|---|---|---|---|
| Ethanol | 78.3 | 78.2 | 96:4 |
| 1-Propanol | 97.2 | 87.7 | 72:28 |
| 2-Propanol | 82.4 | 80.4 | 88:12 |
| 1-Butanol | 117.8 | 92.4 | 62:38 |
| 2-Butanol | 99.5 | 88.5 | 68:32 |
| 2-Methyl-1-propanol | 108 | 90 | 67:33 |
| 2-Methyl-2-propanol | 83 | 80 | 88:12 |

Methanol does not form an azeotrope, but when distilled with water gives a distillate containing 75% methanol and 25% water, which is in proportion to the vapor pressures of the two ingredients.

Inert hydrocarbons such as benzene or toluene that form ternary azeotropes with alcohols and water can also be included in the reaction mixtures used in this invention. This is a modification that is useful when the process is carried out on a large scale. For example, in the preparation of ethyl glycosides of amino sugars, the commercially available benzene denatured ethyl alcohol can be used as the reactant alcohol. In this case the distillate from the reaction mixture can be mixed with excess benzene, distilled to remove water, and the benzene-ethyl alcohol mixture recycled to the reaction mixture. The following Table II lists lower aliphatic alcohols that form ternary azeotropes with water and benzene.

TABLE II

Azeotropes of Alcohols, Water and Benzene (bp. 80.2° C.)

| Alcohol | B.P. of Alcohol °C. | B.P. of Ternary Azeotrope, °C. | Ratio of Alcohol: Water: Benzene |
|---|---|---|---|
| Ethanol | 78.3 | 64.8 | 18.5:7.4:7-4.1 |
| 1-Propanol | 97.2 | 68.5 | 9.0:8.6:-82.4 |
| 2-Propanol | 82.4 | 66.5 | 18.7:7.5:7-3.8 |
| 2-Butanol | 99.5 | 69.0 | 5.8:8.6:8-5.6 |
| 2-Methyl-2-propanol | 83.0 | 67.3 | 21.4:8.1:7-0.5 |

A variety of acid catalysts can be used in the process of this invention. Examples of such catalysts include phosphoric acid, sulfamic acid, sulfuric acid, hydrogen chloride, and acid ion exchange resins. Acids that are insoluble in the reaction mixture are preferred. Examples of operable acid ion exchange resins include the following known commercially as "Amberlite" IR-120 H+, IRC-50 H+, and XE-89 H+. Insoluble acid catalysts have the advantage of being capable of reuse in successive reactions. By way of illustration the catalyst filtered from the reaction mixture can be used as 80–90% of the catalyst charge for the next reaction with 10–20% of fresh catalyst added. The amount of acid ion exchange resin catalyst used can vary widely, proportions ranging from 50% to 100% of the weight of the N-acylglucosamine reactant are satisfactory.

As indicated above the temperature at which the reaction is carried out can range from 30° to 100° C. However, the preferred range is 30°–80° C. since these lower temperatures cause minimal formation of undesirable byproducts.

The resulting alkyl glycoside of the amino sugar is isolated from the reaction mixture by conventional means. Thus, for example, the reaction mixture can be filtered, either warm or after cooling to room temperature, to remove the insoluble catalyst. The catalyst is preferably washed with a small portion of reactant alcohol and the washings combined with the filtrate, which is then evaporated to dryness. The resulting solid alkyl glycoside of the amino sugar, or as alternately named the alkyl 2-acetamidoglycopyranoside, can be used directly, or if desired can be purified by recrystallization from a solvent such as an alcohol or ketone.

DETAILED DESCRIPTION OF PREFERRED EMBODIMENTS

The best modes contemplated for carrying out the process of this invention are illustrated by the following examples:

EXAMPLE I

A mixture of 5.0 g of N-acetyl-D-glucosamine, 5.0 g of the acid ion exchange resin known as "Amberlite" IR-120 H+, and 150 ml of 1-propanol is placed in a glass reaction vessel fitted with a distillation head, and the mixture heated rapidly, with stirring by a magnetic stirrer, to the boiling point (97° C.). Heating is continued with slow distillation of the water-propanol azeotrope from the reaction zone. Distillation is continued until the N-acetyl-D-glucosamine is in solution, 2 hours being required. Distillation is continued for another ½ hour to ensure complete reaction. Approximately 30 ml of water-propanol mixture is distilled from the reaction mixture during this period. The reaction mixture is filtered warm to remove the resin catalyst. The catalyst is washed with 25 ml of 1-propanol and the washings added to the filtrate which is then evaporated to dryness. The product, 1-propyl N-acetyl-D-glucosaminide, amounts to 4.9 g (83% conversion), m.p. 138°–143° C., with an optical rotation $[\alpha]_D$ of +75°.

The ratio of the α-anomer to the β-anomer in an alkyl glycoside of an amino sugar is readily calculated from the measured optical rotation of the product and the optical rotations of the known pure α- and β-anomers, since optical rotation is an additive quantity. The equations which are used for such calculations are as follows:

$$x[\alpha]_D^\alpha + y[\alpha]_D^\beta = [\alpha]_D^{mix}$$

where x = fraction of α-anomer  y = fraction of β-anomer  x+y=1 (for a 2-component mixture)  y=1−x  $[\alpha]_D^\alpha$ = optical rotation of α-anomer  $[\alpha]_D^\beta$ = optical rotation of β-anomer  $[\alpha]_D$mix = optical rotation of mixture of anomers Using these equations, the ratio of α-anomer of 1-propyl N-acetylglucosaminide to the β-anomer in the product of Example I is 70:30, using the known values of $[\alpha]_D$ for the α-anomer of +140.2° and of $[\alpha]_D$ for the β-anomer of −37.1°.

EXAMPLE II

A mixture of 50 g of N-acetyl-D-glucosamine, 40 g of "Amberlite" IR-120 H+ and 1600 ml of 1-propanol is placed in a reaction vessel with a distillation head, and heated with stirring for 3½ hours during which time 100 ml of 1-propanol-water mixture is distilled off. The reaction mixture is cooled to room temperature, and the acid resin filtered out. The resin is washed with a small amount of 1-propanol and the washings added to the filtrate, which is then evaporated to dryness. There is obtained 55 g (93% conversion) of solid 1-propyl N-acetyl-D-glucosaminide having an $[\alpha]_D$ of $+65°$. This indicates an $\alpha$- to $\beta$-anomer ratio of 57.5:42.5. This crude product is dissolved in 200 ml of methanol, the solution filtered to remove unreacted N-acetyl-D-glucosamine, and purified 1-propyl N-acetyl-D-glucosaminide is precipitated out of the methanol solution by addition of methyl ethyl ketone. The purified product amounts to 33.4 g (58% of theory), has a m.p. of 138°–152° C., and optical rotation $[\alpha]_D = +60°$. This rotation indicates an $\alpha$- to $\beta$-anomer ratio of 55:45.

A purified composite sample of 1-propyl N-acetyl-D-glucosaminide having an optical rotation $[\alpha]_D$ of $+69°$ is prepared from a number of runs carried out by the procedures described in Examples I and II. In each of these runs the crude reaction product is dissolved in methanol, the resulting solution filtered to remove insoluble, unreacted N-acetyl-D-glucosamine, and the filtrate treated with methyl ethyl ketone to precipitate 1-propyl N-acetyl-D-glucosaminide. The precipated heart fractions from all runs are dried and combined to form a large, purified sample for use in desired applications. Analysis: 5.54% N; Calcd. 5.34% N; melting point 152°–161° C.

EXAMPLE III

A mixture of 5.0 g of N-acetyl-D-glucosamine, 5.0 g of "Amberlite" IR-120 H+ and 150 ml of methanol is placed in a reaction vessel of the type used in Example I. The reaction mixture is heated with slow distillation at 62° C. until all the N-acetyl-D-glucosamine goes into solution, 1½ hours being required. Reaction is continued for another ½ hour. During the entire distillation approximately 40 ml of water-menthol mixture is removed. After working up in the same manner as described in Example I, there is obtained 4.9 g (93% conversion) of white, solid methyl N-acetyl-D-glucosaminide, m.p. 165°–167° C., $[\alpha]_D$, $+46°$. On the basis of the $\alpha$-anomer having $[\alpha]_D$ of $+131.5°$, and the known $\beta$-anomer having $[\alpha]_D$ of $-44.3°$, the ratio of $\alpha$-anomer to $\beta$-anomer is 50:50.

The products from three runs carried out as described in Example III are combined and dried in vacuo over phosphorus pentoxide for 24 hours, and then in vacuo at 60° C. for 1 hour, m.p. 165°–174° C.; Anal. 5.98% N; Calcd. for methyl glucoside of N-acetyl-D-glucosamine, 5.96% N. Optical rotation of combined sample is $[\alpha]_D + 45°$. This indicates an $\alpha$- to $\beta$-anomer ratio of 50:50.

EXAMPLE IV

Using the procedure described in the preceding Examples, a mixture of 5.0 g of N-acetyl-D-glucosamine, 5.0 g of "Amberlite" IR-120 H+ and 150 ml of 2-propanol is heated to boiling (82° C.) with slow distillation of byproduct water and 2-propanol from the reaction zone. The N-acetyl-D-glucosamine goes into solution in 5 hours. Durig this period approximately 30 ml of water-2-propanol mixture is distilled out. After working up as in the preceding Examples there is obtained 2.3 g (40% conversion) of 2-propyl N-acetyl-D-glucosaminide, $[\alpha]_D = +82°$ C. A smaller amount of yellow gum is formed in this Example than in Example I, despite the longer reaction time.

EXAMPLE V

A mixture of 50 g of N-acetyl-D-glucosamine, 50 g of "Amberlite" IR-120 H+ and 1500 ml of absolute ethanol and 1000 ml of benzene is heated to boiling (77° C.) in a reaction vessel with slow distillation of byproduct water and ethanol from the reaction zone during a period of 2¼ hours. The reaction mixture is cooled to room temperature and the catalyst is filtered out. The catalyst is washed with a little alcohol and the washings added to the filtrate which is then evaporated to dryness at 40° C. The resulting solid amounts to 49.7 g (88% conversion) and is ethyl N-acetyl-D-glucosaminide having an optical rotation $[\alpha]_D$ of $+73°$ fading to $+67°$ (thus indicating the presence of a small amount of N-acetyl-D-glucosamine. The ratio of $\alpha$-anomer to $\beta$-anomer is estimated to be 65:35. The crude product is dissolved in 250 ml of methanol which is filtered to remove insoluble N-acetyl-D-glucosamine. The filtrate is added to 250 ml of methyl ethyl ketone and the mixture evaporated to a volume of 100 ml. This residue is added to 200 ml of methyl ethyl ketone, and the resulting precipitate is filtered out, yielding 33.6 g of ethyl N-acetyl-D-glucosaminide having $[\alpha]_D$ of $+64°$. On the basis of the $\alpha$-anomer having $[\alpha]_D$ of $+134°$ and the $\beta$-anomer having $[\alpha]_D$ of $-42.5°$, the purified product has an $\alpha$:$\beta$ ratio of 60:40.

The significant improvement in the yields of the desirable $\beta$-anomers of the alkyl glycosides of amino sugars obtained by the process of this invention is evident from a comparison of the proportions of $\alpha$- and $\beta$-anomers produced in the above Examples with the proportions of these anomers produced by the reflux method of Zilliken (ibid.). These values are listed in Table III.

TABLE III

| Preparation of Alkyl Glycosides of Amino Sugars | | |
|---|---|---|
| | Ratios of $\alpha$-anomer to $\beta$-anomer | |
| Alkyl | Reported by Zilliken | Obtained in Examples |
| Methyl | 85:15 | 50:50 (Ex. III) |
| Ethyl | 92:8 | 65:35 (Ex. V) |
| n-Propyl | 70:30 | 62.5:37.5 (Exs. I & II avg.) |

The alkyl glycosides of amino sugars obtained by the process of this invention are especially useful as growth promoters for *L. bifidus,* since it is known that the $\beta$-anomers of the alkyl glycosides of amino sugars are more active promoters than the $\alpha$-anomers, and since this process produces higher proportions of the more desirable $\beta$-anomers. Mixtures of different alkyl glycosides of amino sugars are also useful as growth promoters for *L. bifidus.* For example, addition of the $\alpha$-anomer of methyl D-glucosaminide to the $\beta$-anomer of methyl D-glucosaminide or to the $\beta$-anomer of higher alkyl D-glucosaminides enhances the activity of these alkyl glycosides for this purpose.

In addition to their usefulness as growth promoters for *L. bifidus,* the alkyl glycosides of amino sugars are also useful in promoting the healing of wounds. For example, they can be used in treatment of burns, skin inflammation, and psoriasis. They also can be used as promoters of *L. bifidus* growth for use in the treatment of liver disorder. Another use for the alkyl glycosides of amino sugars is for application to hair to control its growth.

It is apparent that changes and modifications may be made without departing from the invention in its broader aspects. The aim of the appended claims, therefore, is to cover all such changes and modifications as fall within the true spirit and scope of the invention.

We claim:

1. The process for improving the proportions of β-anomers in the complex chiral α- and β-anomers formed in the reaction of an N-acylpyranosamine with an aliphatic alcohol having 1-4 carbon atoms in the presence of an acidic ion exchange resin catalyst which comprises carrying out the reaction at a temperature between 30° C. and 100° C. with continuous removal from the reaction zone by distillation the water formed as a by-product.

2. 2-Propyl N-acetyl-D-glucosaminide.